United States Patent [19]
Nordfang et al.

[11] Patent Number: 5,610,278
[45] Date of Patent: Mar. 11, 1997

[54] PROCESS FOR PRODUCING A COAGULATION ACTIVE COMPLEX OF FACTOR VIII FRAGMENTS

[75] Inventors: Ole Nordfang, Hillerød; Mirella E. Rasmussen, Copenhagen, both of Denmark

[73] Assignee: Novo Nordisk A/S, Bagsvaerd, Denmark

[21] Appl. No.: 383,034

[22] Filed: Feb. 3, 1995

Related U.S. Application Data

[63] Continuation of Ser. No. 65,702, May 21, 1993, which is a continuation of Ser. No. 869,885, Apr. 14, 1992, abandoned, which is a continuation of Ser. No. 298,465, Jan. 18, 1989, abandoned, which is a division of Ser. No. 162,323, Feb. 23, 1988, abandoned, which is a continuation-in-part of Ser. No. 932,923, Nov. 19, 1986, abandoned, and a continuation of PCT/DK87/00080, Jun. 24, 1987.

[30] Foreign Application Priority Data

Jun. 24, 1986 [DK] Denmark .................................. 2957/86

[51] Int. Cl.⁶ ........................ A61K 38/37; C07K 14/745; C07K 14/755

[52] U.S. Cl. .......................... 530/383; 530/381; 930/100; 435/69.6

[58] Field of Search .................... 530/383, 381; 514/12; 930/100; 435/69.6

[56] References Cited

FOREIGN PATENT DOCUMENTS 52874   5/1982   European Pat. Off. .

OTHER PUBLICATIONS

D. N. Fass, et al., *Blood* 59(3):594–600 (1982).
D. L. Eaton, et al., *Progress in Hemostasis and Thrombosis* 8:47–70 (1986).

*Primary Examiner*—Dian C. Jacobson
*Attorney, Agent, or Firm*—Steve T. Zelson, Esq.; Cheryl H. Argis, Esq.

[57] ABSTRACT

A coagulation active complex of Factor VIII fragments is produced by causing coagulation inactive FVIII heavy chain to react with coagulation inactive FVIII light chain in the presence of a complex forming agent. Thus, FVIII-HC and FVIII-LC are converted to coagulation active FVIII complex in the presence of divalent metal ions, such as $Mn^{2+}$, $Ca^{2+}$ or $C^{2+}$, or a component of the pro-thrombin complex.

1 Claim, 1 Drawing Sheet

| 1 | 2 | 3 | kD |
|---|---|---|----|
| ■ |   | ─ | 205 |
|   |   | ■ |     |
| ─ | ─ | ═ | 116 |
|   | ─ | ■ | 95 |
| ■ | ─ |   | 66 |
|   | ─ |   | 45 |
|   | ─ |   |    |

PROCESS FOR PRODUCING A COAGULATION ACTIVE COMPLEX OF FACTOR VIII FRAGMENTS

This is a continuation application of co-pending application Ser. No. 08/065,702, filed May 21, 1993, which is a continuation of Ser. No. 07/869,885, filed Apr. 14, 1992 now abandoned, which is a continuation of Ser. No. 07/298,465, filed Jan. 18, 1989, now abandoned, which is a divisional of Ser. No. 07/162,323, filed Feb. 23, 1988, now abandoned, which is a continuation-in-part of Ser. No. 06/932,923, filed Nov. 19, 1986, now abandoned, and a continuation of PCT/DK87/00080, filed Jun. 24, 1987, now abandoned, all of which are incorporated herein by reference in their entirety.

The present invention concerns a process for in vitro production of a coagulation active complex of Factor VIII (FVIII) from inactive FVIII fragments.

Factor VIII is a protein occurring naturally in blood.

It participates as a cofactor in the conversion of Factor X (FX) to activated FX (FXa). The presence of FVIII increases the FXa generation rate about 200,000 times (Dieijen et al, J. Biol. Chem. 156, p. 3433, 1981). Lack of FVIII (hemophilia A) manifests itself as uncontrolled bleedings.

The role of FVIII in the coagulation cascade appears from the following scheme:

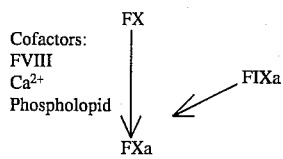

FVIII may be activated by thrombin or FXa and be inactivated by thrombin, FXa or protein C.

Hemophilia A patients are treated with FVIII preparations, either prophylactically or acutely in case of bleedings.

FVIII can be recovered from human blood plasma in which about 1 ppm of the protein is FVIII. Human blood plasma is expensive and the supply is limited. Therefore it is desirable to produce biosynthetic FVIII in cell culture. Three groups have reported successful cloning and expression of human FVIII (Wood et al, Nature, p. 330, 1984—Toole et al, Nature 312, p. 342, 1984—Truet et al, DNA 4, p. 333, 1985).

2 mg of foreign protein/ml can be produced in cell culture. For FVIII this would correspond to 20,000 units/ml. This level far exceeds what has been described for FVIII in the literature. One of the reasons is that FVIII is a very large protein with a molecular weight of about 330 kd (Vehar et al, Nature 312, p. 337, 1984).

FVIII purified from blood plasma or from cell culture consists of FVIII light chain (FVIII-LC) with a molecular weight of about 80 kd, as well as FVIII heavy chain (FVIII-HC) with a molecular weight of from 92 to 210 kd. The fragments are produced from the 330 kd protein by proteolytic cleavage so that 80 kd FVIII-LC is the C terminal fragment, while FVIII-HC is the N-terminal fragment whose size depends upon the degree of proteolytic cleavage.

Thus, it is known that coagulation active FVIII consists of an 80 kd fragment and a fragment with a molecular weight of 92 kd or more (Fulcher and Zimmerman, Symposium on FVIII, Scripps Clinic, 1982).

It would be an advantage to produce FVIII from smaller fragments if there fragments in vitro could be combined to coagulation active FVIII. The fragments could more easily be produced biosynthetically in large amounts because of their smaller size with respect to intact FVIII. Further, the production of FVIII from fragments would be advantageous with a view to subsequent purification from cell culture as the product changes charge and molecular weight by the complex formation.

Experiments have shown that simple combination of the fragments does not provide coagulation active products. Nor does the literature describe methods or conditions which would enable fragments of FVIII to be converted to a coagulation active complex.

The present invention is based on the finding that a coagulation active complex is produced when coagulation inactive FVIII-HC is caused to react with coagulation inactive FVIII-LC in the presence of a complex promoting agent. This is quite surprising because the literature reports purification of FVIII-LC and FVIII-HC (Fass et al, Blood 59, p. 594, 1982—Zimmerman and Fulcher, U.S. Pat. No. 673, 916), without reporting any attempted activity creating combination, notwithstanding that activity creation by combination might have great theoretical and practical importance.

Burke et al (Abstract 14 p. 111. Research in clinic and laboratory 16, 1986) have been able to produce coagulation active FVIII in vivo with cells transfected with DNA for both FVIII-LC and FVIII-HC. However, it was not possible to obtain coagulation activity by mixing culture supernatants which contained FVIII-LC and FVIII-HC, respectively, even though various conditions were tried.

FVIII-LC can be purified from human plasma and has no coagulation activity (Nordfang and Ezban PCT/DK85/00105). FVIII-HC fragments can also be purified from blood plasma (Truett et al, DNA 4, p. 333, 1985). Also these fragments are without coagulation activity.

According to the invention, one or more divalent metal ions are preferably used as complex promoting agents. Examples of suitable agents of this type are $Mn^{2+}$, $Ca^{2+}$ and $Co^{2+}$. Other suitable complex promoting agents are FIXa and FX. If desired, a mixture of these agents may be used.

DEFINITIONS

FVIII-LC or FVIII light chain is a fragment from the C terminal domain of full length FVIII. The molecular weight of the fragment is typically about 80 kd, but may be 70 kd or less. The fragment with the molecular weight of 80 kd has immunological reactivity in the described assay for FVIII-LC antigen and not in assay for FVIII-HC antigen.

FVIII-HC or FVIII heavy chain is a fragment from the N terminal domain of full length FVIII. The molecular weight of the fragment is typically 92 kd, but may be less or up to 210 kd. FVIII-HC purified from plasma consists of a mixture with a molecular weight of 92 to 210 kd. The fragment with a molecular weight greater than or equal to 92 kd has immunological reactivity in the described assay for FVIII-HC antigen but not in assay for FVIII-LC antigen.

Coagulation active FVIII is a protein which is capable of reducing the coagulation time of hemophilia A plasma in coagulation assay. Coagulation active FVIII is moreover capable of promoting the formation of FXa in Coatest assay and thus of converting the chromogenic substrate S2222. Coagulation activity is stated as FVIII:C.

Prothrombin complex is coagulation factors containing α-carboxyglutamic acid, i.e. FII, FVII, FIX, FX, protein C or activated forms of these coagulation factors (Davie et al, Advances in enzymology 48 p. 277, 1979).

METHODS

Coatest assay for FVIII:C

In this assay, FVIII:C is measured in a system consisting of FIXa, FX, $Ca^{2+}$ and phospholipid (PL) (Rosen et al, Thromb Haemostas 54 p. 818, 1985). FXa is formed in an amount depending upon the amount of FVIII:C. The assay is performed as indicated below:

Coatest assay for FVIII:C

1. A 50 μl sample is mixed with 50 μof activation reagent (mixture of FIXa/FX and PL). Incubation time 10 min., 22° C.
2. 25 μl of 25 mM $CaCl_2$ is added, and the mixture is incubated for 20 minutes at 22° C.
3. 50 μl of chromogenic substrate (S2222) for FXa is added.
4. After incubation for 15 min. citric acid is added, and $E_{405}$ of the sample is read.

It is not possible in the Coatest assay to follow an enzymatic activation of FVIII because FVIII in the assay is activated fully by incubation with FIXa/FX, PL and $Ca^{2+}$.

Immunological quantization of FVIII-LC

FVIII-LC antigen (Ag) is measured in specific immuno-assay (Nordfang et al, Thrmob Haemostas 53, p. 346, 1985). Human inhibitor antibody is coated to microplates, sample is added, and bound FVIII-LC is detected with peroxidase labelled $F(ab')_2$ fragment of human inhibitor IgG. Normal human plasma is used as a standard.

Immunological quantization of FVIII-HC

FVIII-HC antigen (Ag) is measured in specific inhibition assay. Dog inhibitor antibody is coated to microplates with loose wells. Sample and $^{125}$I-labelled FVIII-HC are added.

The amount of FVIII-HC in the sample determines the amount of bound $^{125}$I-FVIII-HC. The standard is FVIII concentrate (FVIII Nordisk) set to contain 1 FVIII-HCAg unit per FVIII:C unit.

The amount of FVIII-LC and FVIII-HC determined by immuno-assay is stated relatively. That is the proportion between unit VIII:C-unit FVIII-LCAg-unit FVIII-HCAg for various types of FVIII is not 1:1:1. However, it is assumed that units of the various assays are comparable, but there may be some difference between VII:C unit, FVIII-LCAg unit and FVIII-HCAg unit for a FVIII sample in which all protein is coagulation active in Coatest.

Determination of molecular weight

Molecular weight is determined by reduced SDS-PAGE (Laemmli, Nature 227 p. 680, 1970).

Production of FVIII

FVIII sample for control tests was produced from FVIII concentrate (Nordiocto/Ezban and Nordfang PCT/DK84/00019) by affinity chromatography on goat anti-vWF Sepharose (Truett et al, DNA 4 p. 333, 1985).

Preparation of VIIII-LC (sample A)

FVIII-LC may be purified from blood plasma by several methods (Nordfang and Ezban PCT/DK85/00105—Nordfang et al, Bari International Conference on FVIII 1985). Here, highly concentrated FVIII-LC is used, prepared by affinity chromatography on monoclonal 47 IgG of Nordiocto. Nordiocto dissolved in 200 ml of buffer A(0.02M imidazole, 0.15M NaCl, 10 mM EDTA, pH 7.4) to a concentration of VIII-LCAg of 110 units/ml was incubated overnight with 7 ml of 47 IgG sepharose (coupled with 9 mg of IgG/ml). The incubation mixture was poured on a column, and eluate was collected. The gel was washed with 40 ml of buffer A and 40 ml of buffer A with a total of 0.65M NaCl. FVIII-LC was eluted with 40 ml of 20 mM imidazole/0.65M NaCl/10 mM EDTA/50% ethylene glycol/pH 7.4. A peak fraction of 4 ml was dialysed to 50 mM imidazole/0.15M NaCl/10% glycerol/0.02% $NaN_3$/pH 7.4. The content of FVIII components in the dialysed sample appears from table 1.

Preparation of FVIII-HC (sample B)

FVIII-HC is produced from a FVIII sample by affinity chromatography on monoclonal 56 IgG Sepharose. 56 IgG binds the FVIII-LC/FVIII-HC complex via FVIII-LC (Nordfang et al, Thromb Haemostas 54 p. 586, 1985). 25 ml of FVIII sample with a content of 405 FVIII-HCAg units/ml were incubated overnight with 1.5 ml of 56 IgG Sepharose (coupled with 4 mg of 56 IgG/ml). The incubation mixture was poured on a column, and eluate was collected. The gel was washed with 5 ml of buffer B (20 mM imidazole/0.15M NaCl/10% glycerol/0.1M lysine/pH 7.4) containing 0.35M $CaCl_2$. Then the gel was washed with 15 ml of buffer B with a total NaCl content of 0.65M followed by 5 ml of buffer B with 10 mM EDTA and 0.02% $NaN_3$ (EDTA buffer). The gel was drained and incubated for 1 hour at room temperature with EDTA buffer. After incubation, FVIII-HC was eluted with 5 ml of EDTA buffer. A peak fraction of 2 ml was dialysed to 50 mM imidazole/0.15M NaCl/10% glycerol/0.02% $NaN_3$/pH 7.4. The content of FVIII components in the dialysed sample appears from table 1.

TABLE 1

| FVIII components in dialysed FVIII-LC sample and FVIII-HC sample | | | |
|---|---|---|---|
| | FVIII:C unit/ml | FVIII-LCAg unit/ml | FVIII-HCAg unit/ml |
| FVIII-LC (sample A) | <0.01 | 770 | 1.8 |
| FVIII-HC (sample B) | <0.01 | 0.1 | 2000 |

DESCRIPTION OF THE FIGURE

Samples A and B were analysed by SDS-PAGE, see the attached FIGURE, in which
Lane 1 contains sample A (4 FVIII-LCAg units),
Lane 2 contains molecular weight markers and
Lane 3 contains sample B(8 FVIII-HCAg units)

The process of the invention will be illustrated below by means of some working examples.

EXAMPLE 1

Samples A and B were each diluted 10 times in buffer C (50 mM imidazole, 0.15M NaCl, 0.1% BSA, pH 7.4). 20 μl of A (1/10) was mixed with 20 μl of B 1/10, 3 μl of 0.15M $MnCl_2$ and 40 μl of buffer C. After 48 hours incubation at 22° C. the incubation mixture contained 1200 m units of VIII:C/ml, measured by Coatest.

The following experiments were performed for comparison purposes

Experiment A

The experiment from example 1 was repeated with the change that 3 μl of buffer C was added instead of 3 μl 0.15M $MnCl_2$. After 48 hours incubation at 22° C., this incubation mixture contained less than 5 m units of VII:C/ml, measured by Coatest.

Experiment B

Sample A was diluted 40 times in buffer C. 80 µl of A (1/40) was mixed with 3 µl of 0.15M MnCl$_2$. After 48 hours incubation, the incubation mixture contained less than 5 units of FVIII:C/ml. Similarly, an incubation mixture with sample B contained less than 5 m units of VII:C/ml.

Experiment C

80 µl of FVIII sample diluted 1000 times in buffer C was mixed with 3 µl of 0.15M MnCl$_2$. After 48 hours incubation, the incubation mixture contained 170 m units of VIII:C/ml. 80 µl of FVIII sample diluted 1000 times in buffer C was mixed with 3 µl of buffer C. After 48 hours incubation, the incubation mixture contained 140 m units of FVIII: C/ml.

EXAMPLE 2

Samples A and B were each diluted 10 times in buffer C. 20 µl of A 1/10 were mixed with 20 µl of B (1/10), 3 µl of 2.2M CaCl$_2$ and 40 µl of buffer C. After 12 days incubation at 22° C., the incubation mixture contained 1300 m units of VIII:C/ml.

The following experiment was performed for comparison purposes

The test was repeated as described above, but with the change that 3 µl of buffer C was added instead of 3 µl of 2.2M CaCl$_2$. After 12 days incubation at 22° C., the incubation mixture contained less than 5 m units of FVIII:C/ml.

EXAMPLE 3

Samples A and B were each diluted 100 times in buffer C. 100 µl of A and 100 µl of B was mixed. 50 µl of the mixture were tested in Coatest, as described above. The mixture contained 1.5 m units/ml. 50 µl of the mixture was moreover tested in a modified Coatest with 1 hour preincubation with FIXa/FX prior to addition of PL. Hereby, the Coatest activity increased to 3.0 m units/ml.

The following experiment was performed for comparison purposes

FVIII sample was diluted 30,000 times in buffer C. 50 µl of diluted sample was tested in Coatest, as described above. The diluted sample contained 3.4 m units/ml. 50 µl of the diluted FVIII sample was moreover tested in modified Coatest with 1 hour preincubation with FIXa/FX prior to addition of Pl. Hereby, the diluted sample contained 3.8 m units/ml.

EXAMPLE 4

When performing an experiment as described in example 1, the incubation mixture contained 1000 m units of VIII:C/ml after 24 hours incubation. When 40 µl of FIXa/FX was added instead of 40 µl of buffer C, the incubation mixture contained 1600 m units/ml after 24 hours incubation.

The following experiments were performed for comparison purposes

Experiment A

The experiment was performed as described in example 1, comparison experiment A. After 24 hours the incubation mixture contained less than 5 m units/ml.

Experiment B

40 µl of FVIII sample diluted 500 times in buffer C was mixed with 40 µl of FIXa/FX and 3 µl of 0.15M Mn$^{2+}$. After 24 hours incubation, the incubation mixture contained 120 m units/ml. When 40 µl of FIXa/FX was replaced by 40 µl of buffer C, the incubation mixture contained 170 m units/ml. When additionally the 3 µl of 0.15M Mn$^{2+}$H was replaced by 3 µl of buffer C, the incubation mixture contained 140 m units/ml.

EXAMPLE 5

Samples A and B were each diluted 20 times in buffer C. 20 µl A 1/20 was mixed with 20 µl B 1/20, 40 µl FIXa/FX and 3 µl 0.15M CaCl$_2$. After 4 hours incubation at 22° C. the incubation mixture contained 199 mU of FVIII:C/ml. If FIXa/FX in the incubation mixture was replaced by 40 µl buffer C, then 43 mU of FVIII:C/ml was measured after 4 hours incubation.

EXAMPLE 6

FVIII-LC and FVIII-HC samples containing 800 U of FVIII-LC:Ag/ml and 850 U of FVIII-HC:Ag/ml respectively, were each diluted 3 times. 20 µl FVIII-LC 1/3 was mixed with 20 µl FVIII-HC 1/3 and 10 µl Me$^{2+}$. In mixture A, Me$^{2+}$ was 25 m Mn$^{2+}$. In mixture B, Me$^{2+}$ was 250 mM Ca$^{2+}$. In mixture C, Me$^{2+}$ was 25 mM Mn$^{2+}$ and 250 mM Ca$^{2+}$. After 24 hours incubation, mixture A contained 10.3 U of FVIII:C/ml, mixture B contained 4.0 U of FVIII:C/ml and mixture C contained 12.9 U of FVIII:C/ml. After 144 hours incubation mixture A contained 6.6 U of FVIII:C/ml, mixture B contained 6.5 U of FVIII:C/ml while mixture C contained 11.9 U of FVIII:C/ml.

EXAMPLE 7

COS cells were transfected with 80 kD-FVIII-LC plasmid described in U.S. application (Chiron CH-48 7729-462?). Culture supernatant containing 870 mU of FVIII-LC:Ag/ml was supplemented with plasma purified FVIII-HC to a final concentration of 20 FVIII-HC:Ag U/ml and Mn$^{2+}$ to a final concentration of 4 mM. After 24 hours incubation at 22° C. the mixture contained 137 mU of FVIII:C/ml. When plasma purified FVIII-LC at a concentration of 1000 mU of FVIII-IC:Ag/ml correspondingly was supplemented with FVIII-HC and Mn$^{2+}$, the incubation mixture contained 33 mU of FVIII:C/ml after 24 hours incubation. When the culture supernatant was supplemented with only Mn$^{2+}$ and not FVIII-HC, the incubation mixture contained less than 2.5 Mu of FVIII:C/ml after 24 hours.

We claim:

1. An isolated coagulation active product comprising a complex of an N-terminal fragment of Factor VIII with a molecular weight from 92,000 to 210,000 and a C-terminal fragment of Factor VIII with a molecular weight of from 70,000 to 80,000 combined with Mn$^{2+}$ or a combination Mn$^{2+}$ and Ca$^{2+}$.

* * * * *